United States Patent
Maeda et al.

(10) Patent No.: US 8,158,919 B2
(45) Date of Patent: Apr. 17, 2012

(54) IMAGE CAPTURING SYSTEM, IMAGE CAPTURING METHOD, AND COMPUTER READABLE MEDIUM

(75) Inventors: Kiyohiro Maeda, Ashigarakami-gun (JP); Hideyasu Ishibashi, Ashigarakami-gun (JP); Hiroshi Yamaguchi, Ashigarakami-gun (JP)

(73) Assignee: Fujifilm Corporation, Tokyo (JP)

( * ) Notice: Subject to any disclaimer, the term of this patent is extended or adjusted under 35 U.S.C. 154(b) by 598 days.

(21) Appl. No.: 12/336,871

(22) Filed: Dec. 17, 2008

(65) Prior Publication Data

US 2009/0159776 A1    Jun. 25, 2009

(30) Foreign Application Priority Data

Dec. 19, 2007   (JP) ................................. 2007-326937

(51) Int. Cl.
*H01L 27/00* (2006.01)
*A61B 5/02* (2006.01)

(52) U.S. Cl. ..................................... 250/208.1; 600/500

(58) Field of Classification Search ............... 250/208.1, 250/214.1, 204, 205, 226, 227.18, 227.2, 250/227.23; 348/223.1, 224.1, 225.1; 600/322–324, 600/473–479, 500–504
See application file for complete search history.

(56) References Cited

U.S. PATENT DOCUMENTS

| | | | | |
|---|---|---|---|---|
| 5,251,021 A * | 10/1993 | Parulski et al. | ............... | 358/500 |
| 7,397,758 B1 * | 7/2008 | Hart et al. | ..................... | 370/208 |
| 2008/0125664 A1 * | 5/2008 | Sakai et al. | ................... | 600/500 |

FOREIGN PATENT DOCUMENTS

| JP | 2007-029555 A | 2/2007 |
|---|---|---|
| JP | 2007-50106 A | 3/2007 |

* cited by examiner

*Primary Examiner* — Georgia Y Epps
*Assistant Examiner* — Don Williams
(74) *Attorney, Agent, or Firm* — Sughrue Mion, PLLC

(57) ABSTRACT

An image capturing system includes an image capturing section that includes a plurality of light receiving elements configured to receive light in a first wavelength range and light in a second wavelength range, a control section that controls the light in the second wavelength range to be received by each of the plurality of light receiving elements more frequently than the light in the first wavelength range, where the light in the second wavelength range has a lower spectral intensity than the light in the first wavelength range, and an image generating section that generates an image by using the light in the first wavelength range received by the plurality of light receiving elements at a given timing and the light in the second wavelength range received by the plurality of light receiving elements at a different timing.

23 Claims, 7 Drawing Sheets

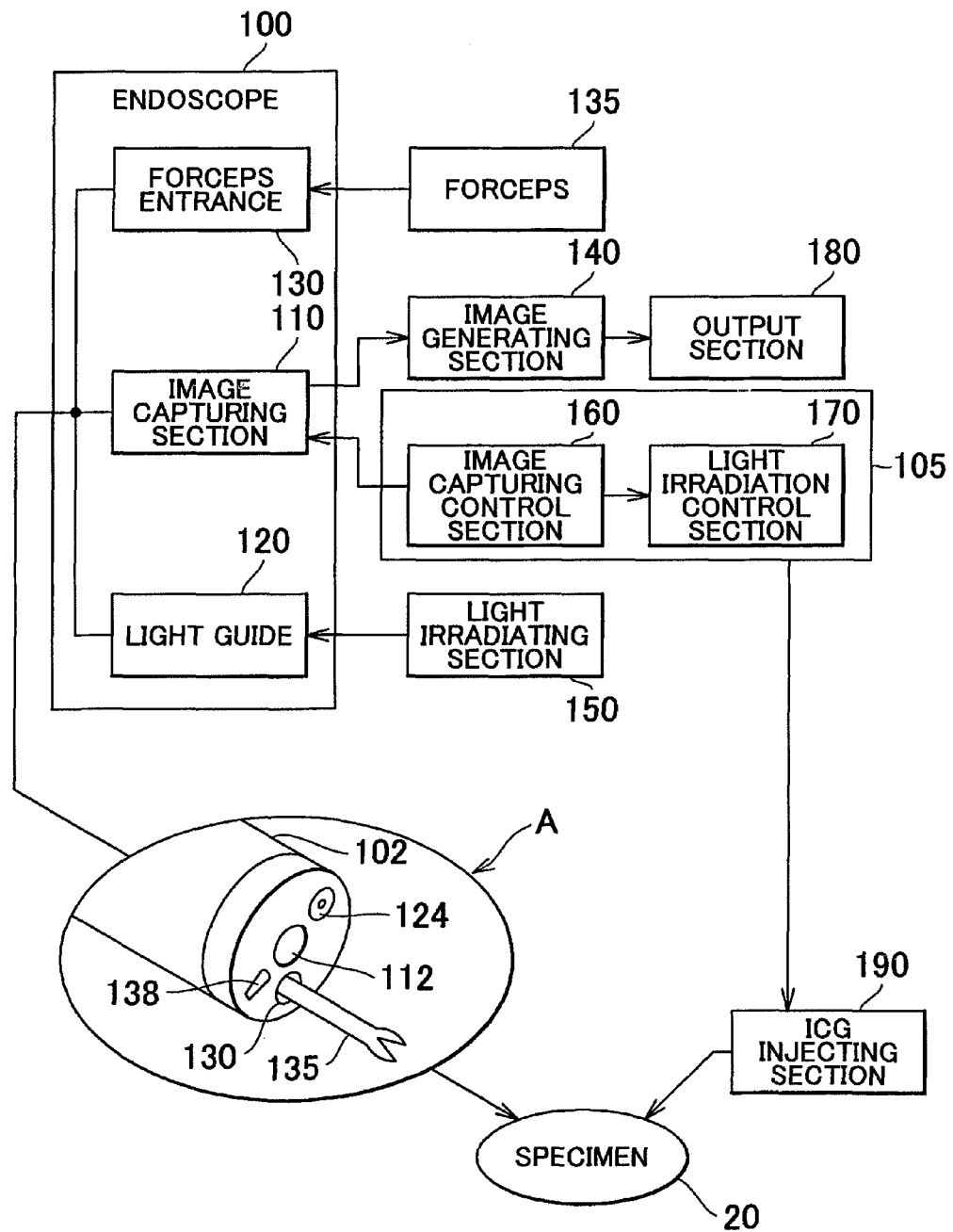
F I G . 1

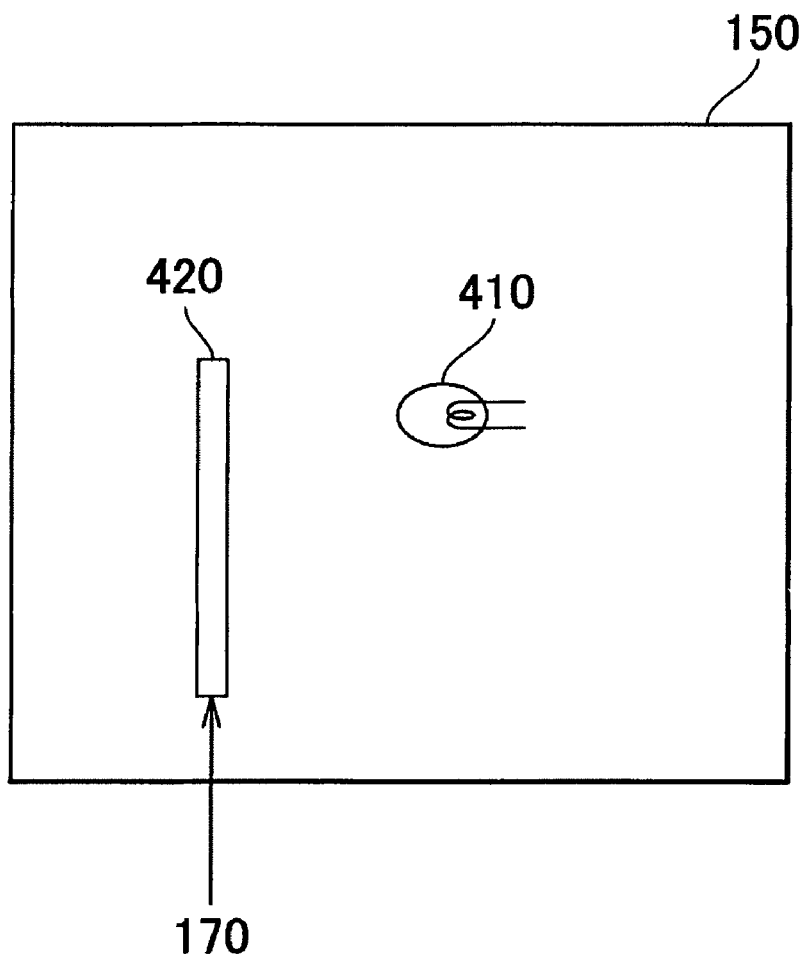
F I G . 3

IMAGE CAPTURING SYSTEM, IMAGE CAPTURING METHOD, AND COMPUTER READABLE MEDIUM

CROSS REFERENCE TO RELATED APPLICATION

The present application claims priority from a Japanese Patent Application No. 2007-326937 filed on Dec. 19, 2007, the contents of which are incorporated herein by reference.

BACKGROUND

1. Technical Field

The present invention relates to an image capturing system, an image capturing method, and a computer readable medium. More particularly, the present invention relates to an image capturing system and an image capturing method for capturing an image and to a computer readable medium for use with the image capturing system.

2. Related Art

A known living organism observing apparatus is capable of capturing high-contrast images of, for example, blood vessels of superficial portions of mucous membranes of living organisms as disclosed in Japanese Patent Application Publication No. 2007-29555, for example. Furthermore, a known electronic endoscope apparatus produces visible images, NBI images, autofluorescence monitoring images with high image quality and sufficient color reproducibility as disclosed in Japanese Patent Application Publication No. 2007-50106, for example.

Many of the images obtained by image-capturing living organisms such as human bodies, especially their inside, may be characterized in that the R component exhibits an extremely higher luminance value than other color components. Here, monitoring images used for, for example, assisting medical doctors to perform procedures essentially require image information regarding the B and G components of the surface of a subject. Since the R component exhibits an extremely high luminance value as mentioned above, however, the image information provided by the B and G components is buried despite of their usefulness for human body observation. In other words, the techniques disclosed in the above two publications suffer from loss of image information provided by light in a wavelength region useful for human body observation.

SUMMARY

Therefore, it is an object of an aspect of the innovations herein to provide an image capturing system, an image capturing method and a computer readable medium which are capable of overcoming the above drawbacks accompanying the related art. The above and other objects can be achieved by combinations described in the independent claims. The dependent claims define further advantageous and exemplary combinations of the innovations herein.

According to the first aspect related to the innovations herein, one exemplary image capturing system may include an image capturing section that includes a plurality of light receiving elements configured to receive light in a first wavelength range and light in a second wavelength range, and a control section that controls the light in the second wavelength range to be received by each of the plurality of light receiving elements more frequently than the light in the first wavelength range, where the light in the second wavelength range has a lower spectral intensity than the light in the first wavelength range.

According to the second aspect related to the innovations herein, one exemplary image capturing method may include capturing an image by using a plurality of light receiving elements configured to receive light in a first wavelength range and light in a second wavelength range, and controlling the light in the second wavelength range to be received by each of the plurality of light receiving elements more frequently than the light in the first wavelength range, where the light in the second wavelength range has a lower spectral intensity than the light in the first wavelength range.

According to the third aspect related to the innovations herein, one exemplary computer readable medium storing thereon a program for use with an image capturing system. When executed, the program causes the image capturing system to function as an image capturing section that captures an image by using (that includes?) a plurality of light receiving elements configured to receive light in a first wavelength range and light in a second wavelength range, and a control section that controls the light in the second wavelength range to be received by each of the plurality of light receiving elements more frequently than the light in the first wavelength range, where the light in the second wavelength range has a lower spectral intensity than the light in the first wavelength range.

The summary clause does not necessarily describe all necessary features of the embodiments of the present invention. The present invention may also be a sub-combination of the features described above. The above and other features and advantages of the present invention will become more apparent from the following description of the embodiments taken in conjunction with the accompanying drawings.

BRIEF DESCRIPTION OF THE DRAWINGS

FIG. 1 illustrates an exemplary configuration of an image capturing system 10 relating to an embodiment of the present invention, together with a specimen 20.

FIG. 3 illustrates an exemplary configuration of a light irradiating section 150.

DESCRIPTION OF EXEMPLARY EMBODIMENTS

Figure 2:
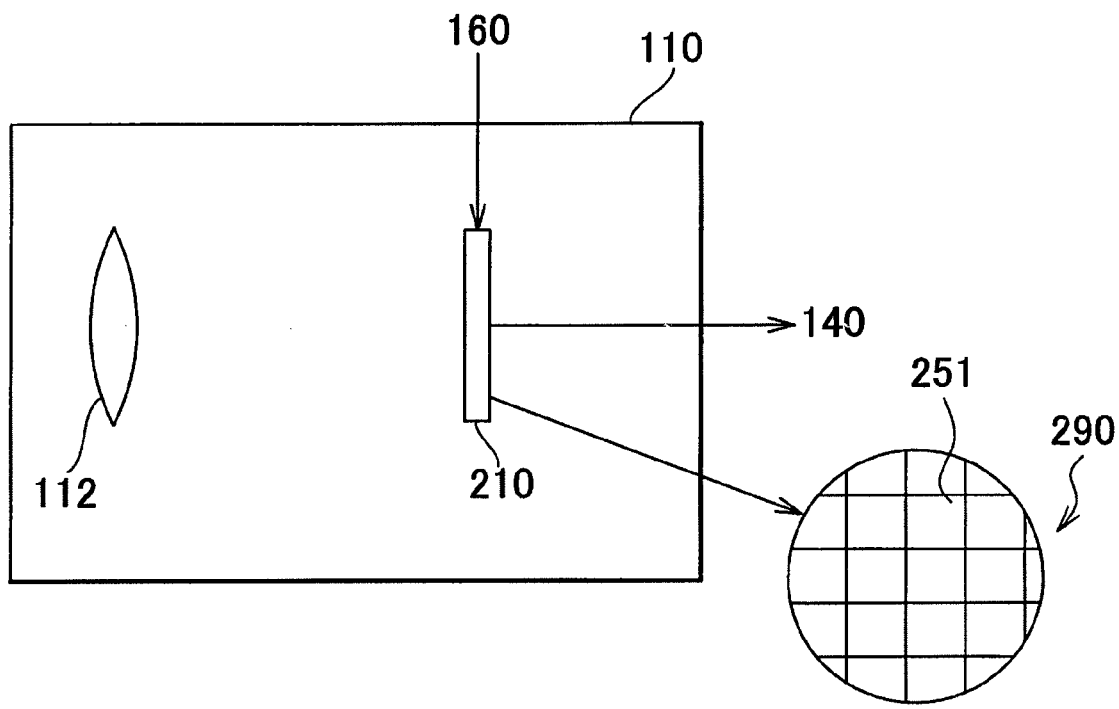
FIG. 2 illustrates an exemplary configuration of an image capturing section 110.

Some aspects of the invention will now be described based on the embodiments, which do not intend to limit the scope of the present invention, but exemplify the invention. All of the features and the combinations thereof described in the embodiment are not necessarily essential to the invention.

FIG. 1 illustrates an exemplary configuration of an image capturing system 10 relating to an embodiment of the present invention, together with a specimen 20. The image capturing system 10 includes an endoscope 100, an image generating section 140, an output section 180, a control section 105, a light irradiating section 150, and an ICG injecting section 190. In FIG. 1, the reference character A indicates an enlargement view of an end portion 102 of the endoscope 100.

The ICG injecting section 190 injects indocyanine green (ICG) into the specimen 20, where indocyanine green serves as an luminescence substance and the specimen 20 is shown as an exemplary subject. In the present embodiment, ICG is introduced as an example of the luminescence substance. Nonetheless, other fluorescent substances than ICG may be used as the luminescence substance.

ICG is excited, for example, by an infra-red ray having a wavelength of 750 nm, to emit fluorescence with a broad spectrum having as its middle a wavelength of 810 nm. When the specimen 20 is a living organism, the ICG injecting section 190 intravenously injects ICG into the blood vessels of the living organism. The image capturing system 10 captures images of the blood vessels of the living organism with the use of the luminescence light emitted from the ICG. Here, the luminescence light includes fluorescence and phosphorescence. The luminescence light, which is shown as an example of the light emitted from the subject, includes luminescence light produced by chemiluminescence, triboluminescence, or thermoluminescence in addition to photoluminescence caused by light such as excitation light.

The ICG injecting section 190 injects ICG into the specimen 20, under the control of, for example, the control section 105, in such a manner that the ICG concentration within the living organism remains substantially constant. The specimen 20 may be a living organism such as a human body, and image-captured to produce images to be processed by the image capturing system 10. In the specimen 20, there are objects such as blood vessels.

The endoscope 100 includes an image capturing section 110, a light guide 120, and a forceps entrance 130. The end portion 102 of the endoscope 100 has a lens 112, which forms a portion of the image capturing section 110. The end portion 102 also has a light exit 124, which forms a portion of the light guide 120. The end portion 102 of the endoscope 100 further has a nozzle 138.

A forceps 135 is inserted into the forceps entrance 130, so that the forceps entrance 130 guides the forceps 135 through the end portion 102. The forceps 135 may have an end with any of various shapes. In addition to forcipes, a variety of treatment tools for treating living organisms may be inserted into the forceps entrance 130. The nozzle 138 sends out water or air.

The light irradiating section 150 generates light to be irradiated through the end portion 102 of the endoscope 100. The light generated by the light irradiating section 150 contains an infra-red ray and irradiation light, where the infra-red ray is shown as an example of excitation light that excites the luminescence substance in the specimen 20 to emit luminescence light and the irradiation light is irradiated to the specimen 20. The irradiation light includes R-component light, G-component light and B-component light, for example.

The light guide 120 is formed by an optical fiber, for example. The light guide 120 is designed to guide the light generated by the light irradiating section 150 to the end portion 102 of the endoscope 100. The light guide 120 may include the light exit 124 formed in the end portion 102. The light generated by the light irradiating section 150 is irradiated to the specimen 20 through the light exit 124.

The image capturing section 110 receives at least one of the light emitted by the luminescence substance and reflection light that is part of the irradiation light reflected by the object.

The image generating section 140 generates an image by processing the light reception data obtained from the image capturing section 110. The output section 180 outputs the image generated by the image generating section 140.

The control section 105 includes an image capturing control section 160 and a light irradiation control section 170. The image capturing control section 160 controls the image capturing operation by the image capturing section 110. The light irradiation control section 170 controls the light irradiating section 150, under the control of the image capturing control section 160. For example, when the image capturing section 110 captures images in a time-sharing manner by using an infra-red ray, R-component light, G-component light, and B-component light, the light irradiation control section 170 controls the light irradiated to the specimen 20 by the light irradiating section 150 in such a manner that the irradiation timing of each component light is synchronized with the image capturing timing.

FIG. 2 illustrates an exemplary configuration of the image capturing section 110. The image capturing section 110 includes the lens 112 and an image capturing device 210. The image capturing device 210 has a plurality of light receiving elements 251. The light receiving elements 251 can receive light in a first wavelength range, light in a second wavelength range, light in a third wavelength range, and light in a fourth wavelength range. In other words, the light receiving elements 251 are sensitive to the light in the first wavelength range, the light in the second wavelength range, the light in the third wavelength range, and the light in the fourth wavelength range. The light receiving elements 251 are arranged in a two-dimensional manner, to form a light receiving element array 290. The first, second, third and fourth wavelength ranges are different from each other, and do not overlap each other.

The first, second, third and fourth wavelength ranges are not limited to the visible light or infra-red light range. For example, however, the first, second, third and fourth wavelength ranges respectively correspond to the R component, the B component, the G component and the IR component. Here, the fourth wavelength range may be the excitation light wavelength range. The light reception data based on the light received by the light receiving elements 251 is supplied to the image generating section 140.

FIG. 3 illustrates an exemplary configuration of the light irradiating section 150. The light irradiating section 150 has a light emitting section 410 and a light-source filter section 420. The light emitting section 410 emits light to be irradiated to the subject. The light emitting section 410 emits light having a wavelength range covering the excitation light wavelength range and the first to third wavelength ranges. The light emitting section 410 may include a xenon lamp. The light receiving elements 251 receive a portion of the light emitted by the light emitting section 410 which is reflected by the subject.

Figure 4:
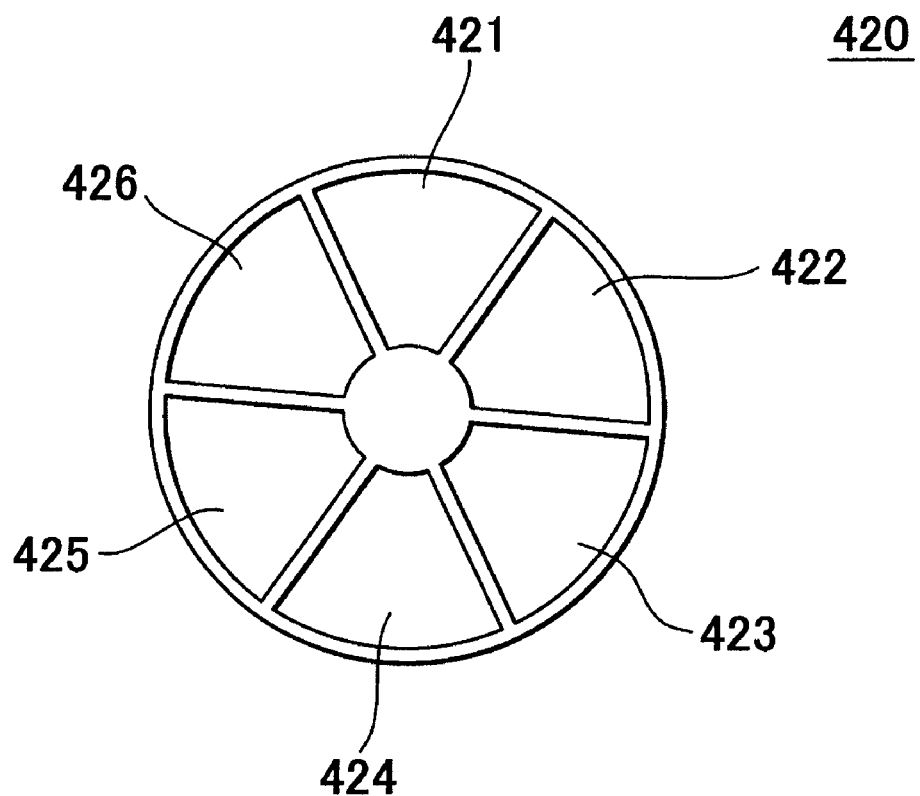
FIG. 4 illustrates an exemplary configuration of a light-source filter section 420.

FIG. 4 illustrates an exemplary configuration of the light-source filter section 420. FIG. 4 illustrates the configuration of the portion of the light-source filter section 420 which faces the light emitting section 410. The light-source filter section 420 includes optical filter sections 421 to 426. The light irradiation control section 170 rotates the light-source filter section 420, around the central axis of the light-source filter section 420, within a plane substantially perpendicular to the direction in which the light emitted by the light emitting section 410 travels.

The optical filter sections 421, 422, 423, 424, 425 and 426 respectively pass light in the first, second, third, fourth, second and third wavelength ranges and cut off light in the other wavelength ranges. Here, the light from the light emitting section 410 is guided to a position off the rotation axis of the light-source filter section 420. Therefore, when the light from the light emitting section 410 is guided to the optical filter section 421, the optical filter section 421 passes light in the first wavelength range, out of the light from the light emitting section 410. At this timing, the light in the first wavelength range is thus irradiated to the subject.

When the light from the light emitting section 410 is guided to the optical filter section 422 or 425, the optical filter section 422 or 425 passes light in the second wavelength range, out of the light from the light emitting section 410. At this timing, the light in the second wavelength range is thus irradiated to the subject. When the light from the light emitting section 410 is guided to the optical filter section 423 or 426, the optical filter section 423 or 426 passes light in the third wavelength range, out of the light from the light emitting section 410. At this timing, the light in the third wavelength range is thus irradiated to the subject. When the light from the light emitting section 410 is guided to the optical filter section 424, the optical filter section 424 passes light in the fourth wavelength range, out of the light from the light emitting section 410. At this timing, the light in the fourth wavelength range is thus irradiated to the subject.

The light receiving elements 251 receive, under the control of the image capturing control section 160, reflection light which is a portion of the irradiated light reflected by the specimen 20 when the light in the first, second and third wavelength ranges is irradiated. Here, the light in the first, second and third wavelength ranges is visible light. The image generating section 140 can generate a visible light image by referring to the amount of the light received by the light receiving elements 251.

In addition, the light receiving elements 251 receive, under the control of the image capturing control section 160, luminescence light emitted by the luminescence substance in the specimen 20 due to the irradiation of excitation light when the light in the fourth wavelength range is irradiated. Here, the light in the fourth wavelength range is excitation light. The image generating section 140 can generate a luminescence light image by referring to the amount of the light received by the light receiving elements 251.

Figure 5:
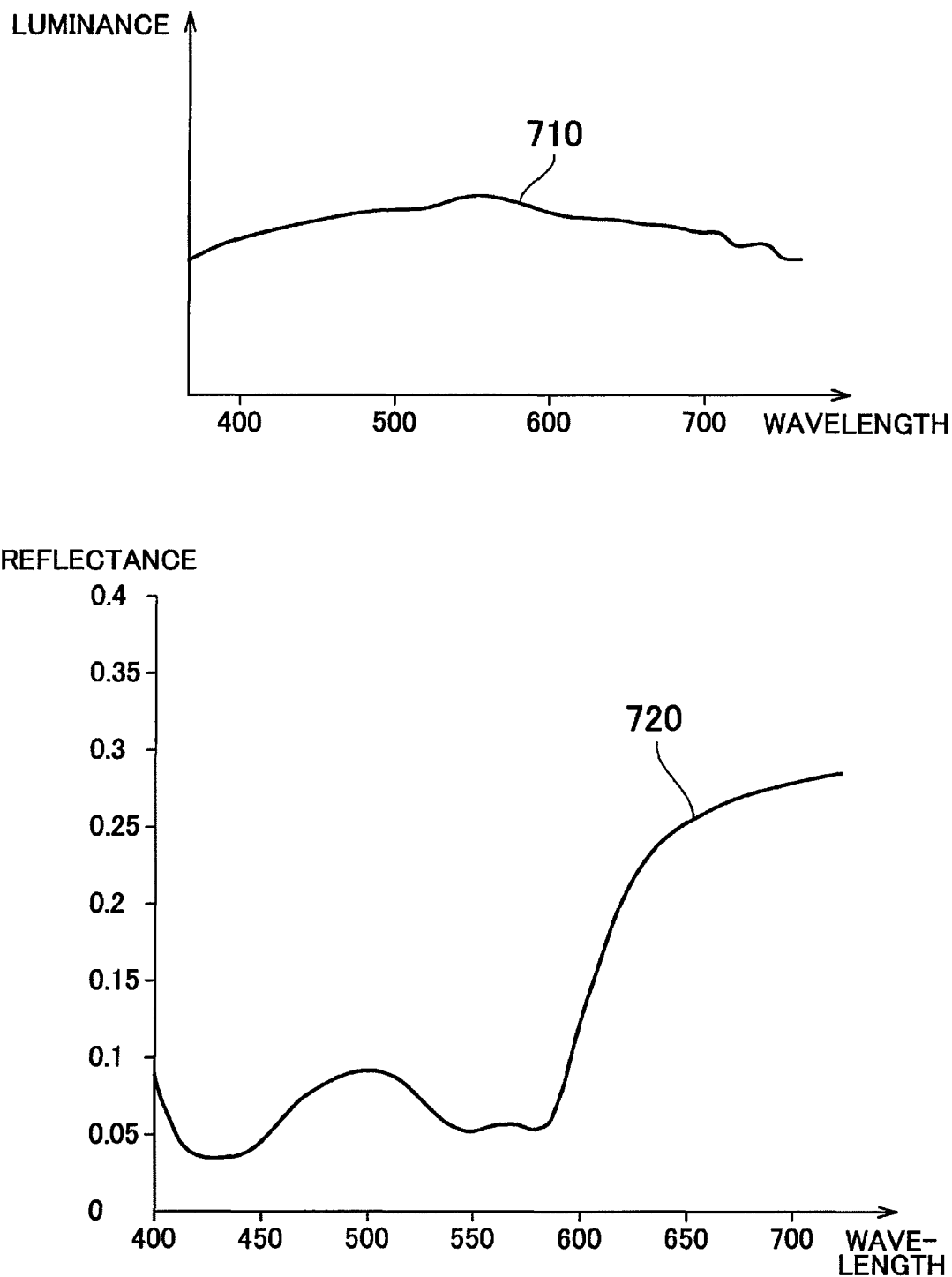
FIG. 5 illustrates, as an example, the spectral intensity of the light irradiated by the light irradiating section 150 and the spectral reflectance of a subject.

FIG. 5 illustrates, as an example, the spectral intensity of the light irradiated by the light irradiating section 150 and the spectral reflectance of the subject. In FIG. 5, a line 710 shows the spectral intensity distribution of light generated by a xenon lamp, which is shown as an example of the light emitting section 410, and exhibits a relatively gentle spectral intensity in the visible light range.

A line 720 shows the spectral reflectance of the mucous membrane of a stomach, which is shown as an example of the subject. As clearly seen from the shown distribution, the spectral reflectance of the subject is lower in the second and third wavelength ranges than in the first wavelength range. The exemplary spectral reflectance and spectral intensity shown in FIG. 5 indicate that the light receiving elements 251 receive light in the first, second and third wavelength ranges at the intensity ratio of 2:1:1. The light irradiation control section 170 controls how frequently light in each wavelength range is irradiated from the light irradiating section 150, according to the intensity of the light in the wavelength range detected by the light receiving elements 251.

For example, the light irradiation control section 170 rotates the light-source filter section 420 at a substantially constant angular speed, and the image capturing control section 160 allows the light receiving elements 251 to receive light while the light from the light emitting section 410 pass through each of the optical filter sections 421 to 426. In this manner, the light irradiation control section 170 controls the light emitting section 410 to generate the light in the second wavelength range more frequently than the light in the first wavelength range, where the spectral reflectance of the subject is lower in the second wavelength range than in the first wavelength range. With such a configuration, the control section 105 enables the light receiving elements 251 to receive the light in the second wavelength range more frequently than the light in the first wavelength range, where the spectral reflectance of the subject is lower in the second wavelength range than in the first wavelength range.

When the light irradiating section 150 irradiates the mucous membrane of the stomach with the light having the spectral intensity shown by the line 710, the reflection light reflected by the mucous membrane of the stomach has a lower spectral intensity in the second wavelength range than in the first wavelength range. Therefore, the control section 105 can control each light receiving element 251 to receive the light in the second wavelength range more frequently than the light in the first wavelength range, where the reflection light has a lower spectral intensity in the second wavelength range than in the first wavelength range.

Here, the product of the spectral reflectance in each wavelength range and the spectral intensity in the wavelength range of the light irradiated to the subject from the light emitting section 410 is proportional to the intensity of the reflection light. Therefore, the light irradiation control section 170 preferably controls the ratio of the frequency with which the light in the second wavelength range is received to the frequency with which the light in the first wavelength range is received so as to be substantially equal to the ratio of the product of the spectral reflectance in the first wavelength range and the spectral intensity in the first wavelength range of the light irradiated to the subject from the light emitting section 410 to the product of the spectral reflectance in the second wavelength range and the spectral intensity in the second wavelength range of the light irradiated to the subject from the light emitting section 410.

Also taking into consideration the light reception sensitivity of the light receiving elements 251, the light irradiation control section 170 may control how frequently the light in each wavelength range is received by the light receiving elements 251, according to an output value associated with each wavelength range, where the output value represents the degree at which the light receiving elements 251 receive the light from the subject and output the received light. In other words, the light irradiation control section 170 controls the ratio of the frequency with which the light in the second wavelength range is received to the frequency with which the light in the first wavelength range is received so as to be substantially equal to the ratio of the product of the spectral reflectance in the first wavelength range, the spectral intensity in the first wavelength range of the light irradiated to the subject from the light emitting section 410 and the light reception sensitivity of the light receiving elements 251 in the first wavelength range to the product of the spectral reflectance in the second wavelength range, the spectral intensity in the second wavelength range of the light irradiated to the subject from the light emitting section 410 and the light reception sensitivity of the light receiving elements 251 in the second wavelength range.

As described above, the light irradiation control section 170 controls the ratio of the frequency with which the light in the second wavelength is received to the frequency with which the light in the first wavelength range is received, in accordance with the ratio of the spectral reflectance in the first wavelength range to the spectral reflectance in the second wavelength range. Specifically speaking, the light irradiation control section 170 may control the ratio of the frequency with which the light in the second wavelength is received to the frequency with which the light in the first wavelength range is received so as to be substantially equal to the ratio of the spectral reflectance in the first wavelength range to the spectral reflectance in the second wavelength range.

By performing the above-described control procedure, the light irradiation control section 170 can enable the light receiving elements 251 to receive the light in the third wavelength range more frequency than the light in the first wavelength range, and control the ratio of the frequency with which the light in the third wavelength range is received to the frequency with which the light in the first wavelength range is received, according to the ratio of the spectral reflectance of the subject in the first wavelength range to the spectral reflectance of the subject in the third wavelength range. To sum up, the light irradiation control section 170 controls how frequently the light receiving elements 251 receive the light in each of the first, second and third wavelength ranges, according to the intensity of the reflection light from the subject.

In the above-described manner, the light irradiation control section 170 controls the light in each wavelength range to be irradiated to the subject at a different timing. The image generating section 140 is provided with the light reception data formed by the light received by the light receiving elements 251 at each timing, and generates an image by using the light in the first wavelength range and the light in the second wavelength range received by the light receiving elements 251 respectively at different timings. For example, the image generating section 140 generates a single image by using the light in the first wavelength range and the light in the second wavelength range received by the light receiving elements 251 at different timings.

Figure 6:
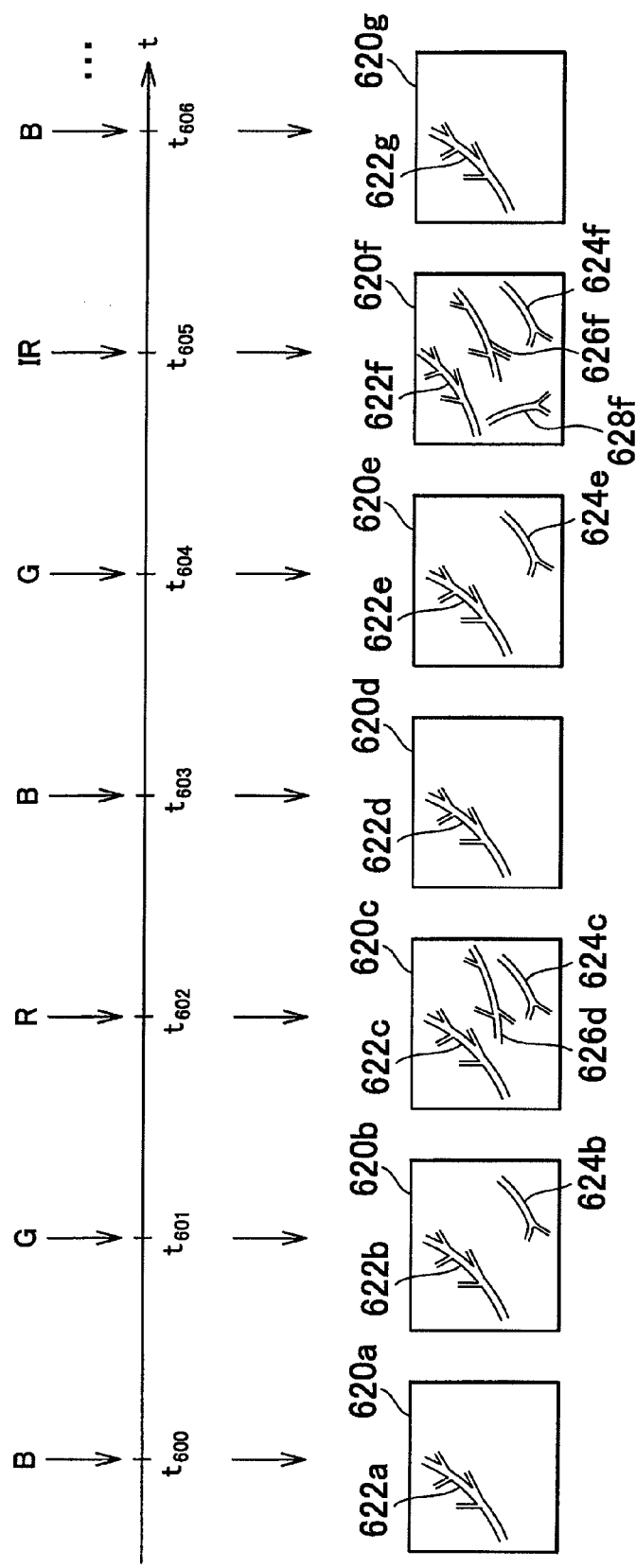
FIG. 6 illustrates exemplary image capturing timings of the image capturing section 110 and exemplary images generated by an image generating section 140.

FIG. 6 illustrates exemplary image capturing timings of the image capturing section 110 and exemplary images generated by the image generating section 140. The image capturing control section 160 allows the image capturing section 110 to capture images at times t600, t601, t602, t603, t604, t605, t606 . . . .

Specifically speaking, the light irradiation control section 170 controls, for example, the rotation of the light-source filter section 420 according to the timing control procedure by the image capturing control section 160, so that the light emitted by the light emitting section 410 is irradiated to the subject through the optical filter sections 422, 423, 421, 425, 426, and 424 respectively at the times t600, t601, t602, t603, t604, t605, and t606. In this manner, at the times t600, t601, t602, t603, t604, t605, and t606, the B-component light, G-component light, R-component light, B-component light, G-component light, and excitation light are irradiated to the subject from the light irradiating section 150.

The image capturing control section 160 controls the light receiving elements 251 to receive the reflection light from the subject for a predetermined duration at each timing. The image capturing control section 160 then supplies the amount of the light received by the light receiving elements 251 to the image generating section 140. For the sake of intelligibility, exemplary images 620a, 620b, 620c, 620d, 620e, 620f and 620g are shown as the images represented by the light received by the light receiving elements 251 at the times t600, t601, t602, t603, t604, t605, and t606.

The image 620a formed by the B-component light includes a blood vessel image 622a, which is an image of a blood vessel at a shallow position. Here, the images 620d and 620g formed by the B-component light also include similar blood vessel images to the image 620a. The image 620b formed by the G-component light may include a blood vessel image 624b in addition to a blood vessel image 622b showing the same blood vessel as the blood vessel image 622a, where the blood vessel image 624b shows a blood vessel at a position that is deeper than the position of the blood vessel shown by the blood vessel images 622a and 622b and that is within a reach of the G-component light. Here, the image 620e formed by the G-component light also includes similar blood vessel images to the image 620b.

The image 620c formed by the R-component light may include a blood vessel image 626c in addition to a blood vessel image 622c showing the same blood vessel as the blood vessel image 622a and a blood vessel image 624c showing the same blood vessel as the blood vessel image 624b, where the blood vessel image 626c shows a blood vessel at a position that is deeper than the positions of the blood vessels shown by the blood vessel images 622a and 622c and the blood vessel images 624b and 624c and that is within a reach of the R-component light. Needless to say, the images 620a to 620e and 620g include surface images formed by reflection light from the surface, in addition to the above-mentioned blood vessel images showing the blood vessels under the surface. The image 620f includes a blood vessel image 628f formed by the luminescence light from a blood vessel at a deep position out of the reach of the R-component light, in addition to blood vessel images 622f, 624f, and 626f formed by the luminescence light from the blood vessels shown by the blood vessel images 622c, 624c, and 626c, where the luminescence light is created by the excitation light in the infra-red range.

The image generating section 140 generates a single visible light image based on the amount of the B-component light received by the light receiving elements 251 at the time t600, the amount of the G-component light received by the light receiving elements 251 at the time t601, and the amount of the R-component light received by the light receiving elements 251 at the time t602. Here, the image generating section 140 may extract blood vessel regions from the images 620a to 620c by using a technique such as pattern matching and generate the single visible light image by overlaying the extracted blood vessel images. Specifically speaking, the image generating section 140 extracts an image of a blood vessel at a shallow position from the image 620a, an image of a blood vessel at a deep position from the image 620c, and an image of a blood vessel at an intermediate position from the image 620b. Consequently, the image generating section 140 can generate a natural visible light image while enhancing the blood vessel positions.

The image generating section 140 can extract, from the image 620f, an image of a blood vessel at a deeper position than the blood vessels shown by the blood vessel images included in the visible light image. Hence, the image capturing system 10 can produce images of blood vessel at deep positions that cannot be included in visible light images. The image generating section 140 may output the image 620f or the blood vessel image extracted from the image 620f, in association with the image-capturing time or the visible light image generated by referring to the amount of the light received by the light receiving elements 251 at a timing in the vicinity of the timing at which the image 620f is captured. The image generating section 140 may combine the image 620f with the visible light image and output the resultant image.

At the time t605, the image capturing section 110 captures an image by using luminescence light, in place of the R-component light. In this case, the image generating section 140 generates a single visible light image based on the amount of the B-component light received by the light receiving elements 251 at the time t603, the amount of the G-component light received by the light receiving elements 251 at the time t604, and the amount of the R-component light received by the light receiving elements 251 at the time t602. In this manner, the image generating section 140 can generate a pseudo visible light image even when a luminescence light image is captured by using the excitation light, in place of the R-component light. The output section 180 successively displays the visible light images generated by the image generating section 140.

When the specimen 20 is a living organism such as a human body, a visible light image is usually characterized in that the R component has a smaller spatial frequency component than the G and B components. For this reason, image degradation is usually less significant when the R-component images are dropped than when the G- and B-component images are dropped. The above-described configuration can thus dramatically reduce the awkwardness in the images, when compared with the case where the G- and B-component images are dropped.

By putting the image capturing system 10 relating to the present embodiment into a practical use, it may become possible to enable medical doctors to observe internal blood vessels, which cannot be visually seen by surface observation while the medical doctors perform operations or the like with their eyes on the images displayed by the output section 180, for example. Furthermore, the medical doctors advantageously can perform operations or the like by referring to visible light images with substantially no images dropped.

The above description is made for an embodiment where the light irradiation control section 170 controls the frequency with which the light in each wavelength range is irradiated from the light irradiating section 150. Alternatively, the image capturing control section 160 may control the frequency with which the light in each wavelength range is received by the light receiving elements 251, by controlling the wavelength range of the light received by the light receiving elements 251. For example, an optical filter having similar transmission characteristics to the light-source filter section 420 (note that the optical filter section 424 is configured to transmit luminescence light) is provided at the light path between the subject and the light receiving elements 251. The image capturing control section 160 rotates the optical filter in a similar manner to the light-source filter section 420. In this manner, the alternative embodiment can control the frequency with which the light in each wavelength range is received by the light receiving elements 251.

In the above description, the frequency may denote the number of times during a unit time at which the light receiving elements 251 receive the light from the subject so that images of the subject are captured. The control section 105 may dynamically control the frequency according to the amount of the light in each wavelength range received by the light receiving elements 251 from the subject.

Figure 7:
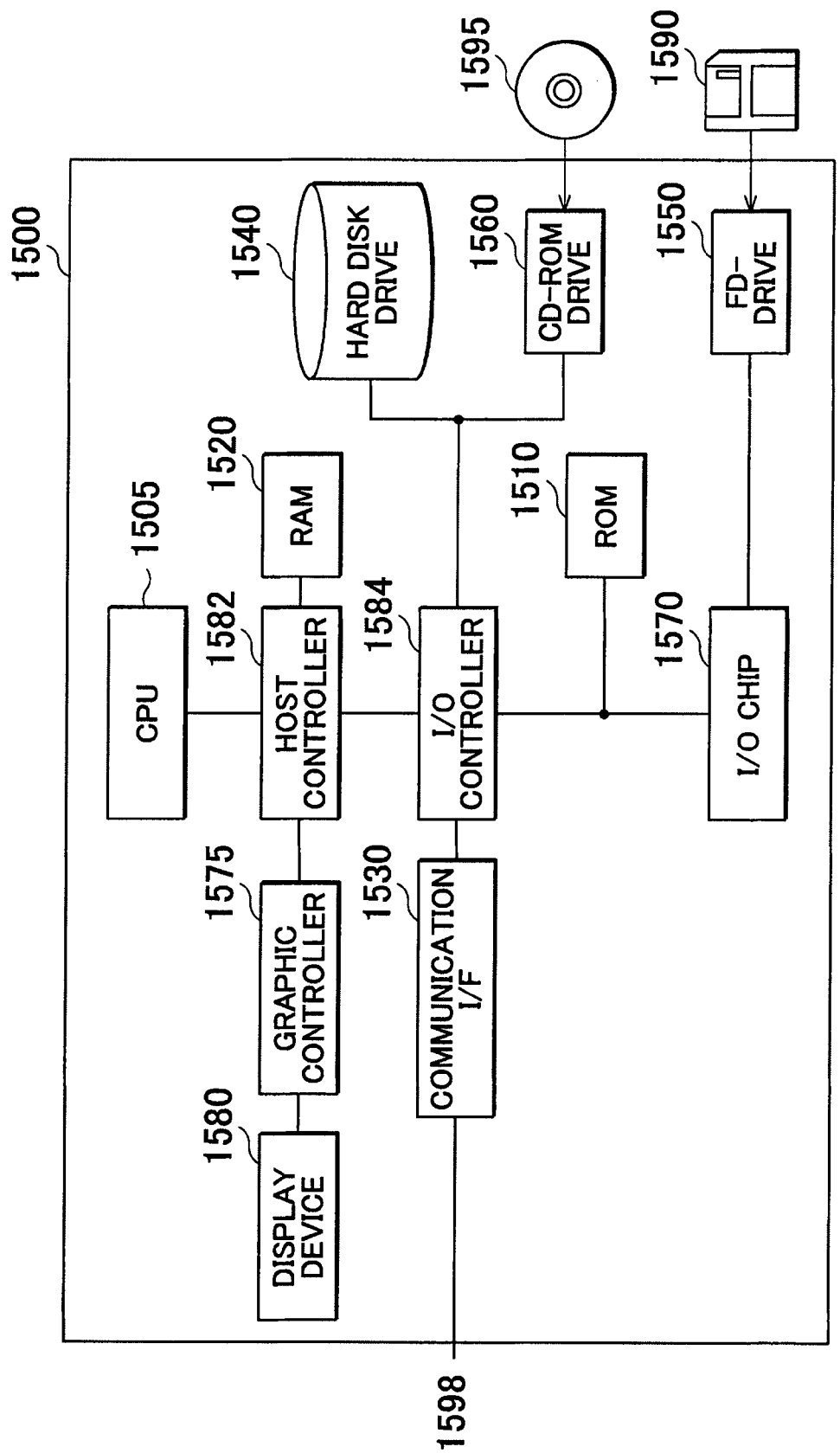
FIG. 7 illustrates an exemplary hardware configuration of a computer 1500 functioning as the image capturing system 10.

FIG. 7 illustrates an exemplary hardware configuration of a computer 1500 functioning as the image capturing system 10. The image capturing system 10 relating to the present embodiment is constituted by a CPU peripheral section, an input/output (I/O) section and a legacy I/O section. The CPU peripheral section includes a CPU 1505, a RAM 1520, a graphic controller 1575 and a display device 1580 which are connected to each other by means of a host controller 1582. The I/O section includes a communication interface 1530, a hard disk drive 1540, and a CD-ROM drive 1560 which are connected to the host controller 1582 by means of an I/O controller 1584. The legacy I/O section includes a ROM 1510, a flexible disk drive 1550, and an I/O chip 1570 which are connected to the I/O controller 1584.

The host controller 1582 connects the RAM 1520 with the CPU 1505 and graphic controller 1575 which access the RAM 1520 at a high transfer rate. The CPU 1505 operates in accordance with programs stored on the ROM 1510 and RAM 1520, to control the constituents. The graphic controller 1575 obtains image data which is generated by the CPU 1505 or the like on a frame buffer provided within the RAM 1520, and causes the display device 1580 to display the obtained image data. Alternatively, the graphic controller 1575 may include therein a frame buffer for storing thereon the image data generated by the CPU 1505 or the like.

The I/O controller 1584 connects, to the host controller 1582, the hard disk drive 1540, communication interface 1530 and CD-ROM drive 1560 which are I/O devices operating at a relatively high rate. The communication interface 1530 communicates with different apparatuses via the network. The hard disk drive 1540 stores thereon programs and data to be used by the CPU 1505 in the image capturing system 10. The CD-ROM drive 1560 reads programs or data from a CD-ROM 1595, and supplies the read programs or data to the hard disk drive 1540 via the RAM 1520.

The I/O controller 1584 is also connected to the ROM 1510, flexible disk drive 1550 and I/O chip 1570 which are I/O devices operating at a relatively low rate. The ROM 1510 stores thereon a boot program executed by the image capturing system 10 at the startup, programs dependent on the hardware of the image capturing system 10, and the like. The flexible disk drive 1550 reads programs or data from a flexible disk 1590, and supplies the read programs or data to the hard disk drive 1540 via the RAM 1520. The I/O chip 1570 is connected to the flexible disk drive 1550, and used to connect a variety of I/O devices to the image capturing system 10, via a parallel port, a serial port, a keyboard port, a mouse port or the like.

The communication programs to be provided to the hard disk drive 1540 via the RAM 1520 are provided by a user in the state of being stored on a recording medium such as the flexible disk 1590, the CD-ROM 1595, and an IC card. The communication programs are read from the recording medium, and the read programs are installed in the hard disk drive 1540 in the image capturing system 10 via the RAM 1520, to be executed by the CPU 1505. The communication programs that are installed in the image capturing system 10 and executed cause the CPU 1505 and the like to cause the image capturing system 10 to function as the image capturing section 110, the image generating section 140, the output section 180, the control section 105 and the light irradiating section 150 described with reference to FIGS. 1 to 6.

Although some aspects of the present invention have been described byway of exemplary embodiments, it should be understood that those skilled in the art might make many changes and substitutions without departing from the spirit and the scope of the present invention which is defined only by the appended claims.

What is claimed is:
1. An image capturing system comprising:
an image capturing section that includes a plurality of light receiving elements configured to receive light in a first wavelength range and light in a second wavelength range; and
a control section that controls the light in the second wavelength range to be received by each of the plurality of light receiving elements more frequently than the light in the first wavelength range, the light in the second wavelength range having a lower spectral intensity than the light in the first wavelength range, wherein the plurality of light receiving elements receive reflection light from inside of a living organism.

2. The image capturing system as set forth in claim 1, further comprising
an image generating section that generates an image by using the light in the first wavelength range received by the plurality of light receiving elements at a given timing and the light in the second wavelength range received by the plurality of light receiving elements at a different timing.

3. The image capturing system as set forth in claim 2, wherein
the control section controls the light in the second wavelength range to be received by the plurality of light receiving elements more frequently than the light in the first wavelength range, where a spectral reflectance of a subject is lower in the second wavelength range than in the first wavelength range.

4. The image capturing system as set forth in claim 2, wherein
the image generating section generates an image by using excitation light in a third wavelength range received by the plurality of light receiving elements at a timing different from the timings at which the lights in the first and second wavelength ranges are received by the plurality of light receiving elements.

5. The image capturing system as set forth in claim 3, wherein
the control section controls a ratio of a frequency with which the light in the second wavelength range is received to a frequency with which the light in the first wavelength range is received, according to a ratio of the spectral reflectance in the first wavelength range to the spectral reflectance in the second wavelength range.

6. The image capturing system as set forth in claim 3, further comprising
a light irradiating section that irradiates the subject with light, wherein
the plurality of light receiving elements receive a portion of the light from the light irradiating section which is reflected by the subject, and
the control section controls the light in the second wavelength range to be irradiated from the light irradiating section to the subject more frequently than the light in the first wavelength range, where the spectral reflectance of the subject is lower in the second wavelength range than in the first wavelength range.

7. The image capturing system as set forth in claim 5, wherein
the plurality of light receiving elements receive light in a third wavelength range that is different from the first and second wavelength ranges,
the spectral reflectance of the subject is lower in the third wavelength range than in the first wavelength range, and
the control section controls the light in the third wavelength range to be received by the plurality of light receiving elements more frequently than the light in the first wavelength range, and controls a ratio of the frequency with which the light in the third wavelength range is received to the frequency with which the light in the first wavelength range is received, according to a ratio of the spectral reflectance in the first wavelength range to the spectral reflectance in the third wavelength range.

8. The image capturing system as set forth in claim 5, wherein
the control section controls the ratio of the frequency with which the light in the second wavelength range is received to the frequency with which the light in the first wavelength range is received so as to be substantially equal to the ratio of the spectral reflectance in the first wavelength range to the spectral reflectance in the second wavelength range.

9. The image capturing system as set forth in claim 8, further comprising
a light irradiating section that irradiates the subject with light, wherein
the control section controls the ratio of the frequency with which the light in the second wavelength range is received to the frequency with which the light in the first wavelength range is received so as to be substantially equal to a ratio of (i) a product of the spectral reflectance in the first wavelength range and a spectral intensity in the first wavelength range of the light irradiated to the subject by the light irradiating section to (ii) a product of the spectral reflectance in the second wavelength range and a spectral intensity in the second wavelength range of the light irradiated to the subject by the light irradiating section.

10. The image capturing system as set forth in claim 9, wherein
the control section controls the ratio of the frequency with which the light in the second wavelength range is received to the frequency with which the light in the first wavelength range is received so as to be substantially equal to a ratio of (i) a product of the spectral reflectance in the first wavelength range, the spectral intensity in the first wavelength range of the light irradiated to the subject by the light irradiating section and a light reception sensitivity of the plurality of light receiving elements in the first wavelength range to (ii) a product of the spectral reflectance for the light in the second wavelength range, the spectral intensity in the second wavelength range of the light irradiated to the subject by the light irradiating section, and a light reception sensitivity of the plurality of light receiving elements in the second wavelength range.

11. The image capturing system as set forth in claim 10, wherein
the plurality of light receiving elements receive reflection light from a living organism, and
the second wavelength range is a blue wavelength range and the first wavelength range is a red wavelength range.

12. The image capturing system as set forth in claim 10, wherein
the plurality of light receiving elements receive reflection light from a human body, and
the second wavelength range is a green wavelength range and the first wavelength range is a red wavelength range.

13. The image capturing system as set forth in claim 11, wherein
the plurality of light receiving elements receive reflection light from a human body.

14. The image capturing system as set forth in claim 13, wherein
the plurality of light receiving elements receive reflection light from a human body having a blood component.

15. The image capturing system as set forth in claim 1, further comprising
a luminescence substance injecting section that injects a luminescence substance into a blood vessel of the living organism.

16. The image capturing system as set forth in claim 1, further comprising a light irradiating section that emits light to be irradiated to the subject and that includes a light emitting section and a light-source filter section, wherein the light-source filter section includes a first optical filter section that passes light in the first wavelength range and cut off light in the other wavelength ranges and a second optical filter section that passes light in the second wavelength range and cut off light in the other wavelength ranges.

17. An image capturing method comprising:

capturing an image by using a plurality of light receiving elements configured to receive light in a first wavelength range and light in a second wavelength range; and controlling the light in the second wavelength range to be received by each of the plurality of light receiving elements more frequently than the light in the first wavelength range, the light in the second wavelength range having a lower spectral intensity than the light in the first wavelength range, wherein the plurality of light receiving elements receive reflection light from inside of a living organism.

18. The image capturing method as set forth in claim 17, wherein an image is generated by using the light in the first wavelength range received by the plurality of light receiving elements at a given timing and the light in the second wavelength range received by the plurality of light receiving elements at a different timing.

19. The image capturing method as set forth in claim 18, wherein the light in the second wavelength range is controlled to be received by the plurality of light receiving elements more frequently than the light in the first wavelength range, where a spectral reflectance of a subject is lower in the second wavelength range than in the first wavelength range.

20. The image capturing method as set forth in claim 19, wherein a ratio of a frequency with which the light in the second wavelength range is received to a frequency with which the light in the first wavelength range is received is controlled according to a ratio of the spectral reflectance in the first wavelength range to the spectral reflectance in the second wavelength range.

21. The image capturing method as set forth in claim 19, wherein light is irradiated to the subject, the plurality of light receiving elements receive a portion of the irradiated light which is reflected by the subject, and the light in the second wavelength range is irradiated to the subject more frequently than the light in the first wavelength range, where the spectral reflectance of the subject is lower in the second wavelength range than in the first wavelength range.

22. The image capturing method as set forth in claim 20, wherein the ratio of the frequency with which the light in the second wavelength range is received to the frequency with which the light in the first wavelength range is received is controlled so as to be substantially equal to the ratio of the spectral reflectance in the first wavelength range to the spectral reflectance in the second wavelength range.

23. A non-transitory computer readable medium storing therein a program for use in an image capturing system, execution of the program causing the image capturing system to function as:

an image capturing section that captures an image by using a plurality of light receiving elements configured to receive light in a first wavelength range and light in a second wavelength range; and a control section that controls the light in the second wavelength range to be received by each of the plurality of light receiving elements more frequently than the light in the first wavelength range, the light in the second wavelength range having a lower spectral intensity than the light in the first wavelength range, wherein the plurality of light receiving elements receive reflection light from inside of a living organism.

* * * * *